(12) United States Patent
Kobayashi et al.

(10) Patent No.: US 12,266,127 B2
(45) Date of Patent: Apr. 1, 2025

(54) MEDICAL SYSTEM, SIGNAL PROCESSING DEVICE, AND SIGNAL PROCESSING METHOD

(71) Applicant: SONY GROUP CORPORATION, Tokyo (JP)

(72) Inventors: Yohei Kobayashi, Tokyo (JP); Yoshio Soma, Tokyo (JP); Keisuke Uyama, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 594 days.

(21) Appl. No.: 17/437,533

(22) PCT Filed: Mar. 12, 2020

(86) PCT No.: PCT/JP2020/010741
§ 371 (c)(1),
(2) Date: Sep. 9, 2021

(87) PCT Pub. No.: WO2020/195877
PCT Pub. Date: Oct. 1, 2020

(65) Prior Publication Data
US 2022/0148209 A1    May 12, 2022

(30) Foreign Application Priority Data
Mar. 25, 2019    (JP) ................. 2019-056683

(51) Int. Cl.
*G06T 7/593* (2017.01)
*G06T 7/00* (2017.01)
*G16H 30/40* (2018.01)

(52) U.S. Cl.
CPC ............ *G06T 7/593* (2017.01); *G06T 7/0012* (2013.01); *G16H 30/40* (2018.01); *G06T 2207/20104* (2013.01)

(58) Field of Classification Search
CPC .................. G06T 7/593; G06T 7/0012; G06T 2207/20104; G16H 30/40
See application file for complete search history.

(56) References Cited

U.S. PATENT DOCUMENTS

| 10,692,219 B2 * | 6/2020 | Hauser ................. A61B 6/4007 |
| 2007/0143066 A1 * | 6/2007 | Floyd ..................... G01N 19/10 |
| | | 702/155 |

(Continued)

FOREIGN PATENT DOCUMENTS

| CN | 105078576 A | 11/2015 |
| CN | 108133495 A | 6/2018 |

(Continued)

OTHER PUBLICATIONS

International Search Report and Written Opinion of PCT Application No. PCT/JP2020/010741, issued on Jun. 2, 2020, 08 pages of ISRWO.

(Continued)

*Primary Examiner* — Lewis G West
(74) *Attorney, Agent, or Firm* — CHIP LAW GROUP

(57) ABSTRACT

The present technology relates to a medical system, a signal processing device, and a signal processing method capable of obtaining highly accurate three-dimensional (3D) information in real time. Further, first 3D information regarding an operative field is generated with a first algorithm by using an operative field image obtained by imaging the operative field. In a case where an area of interest is set in the operative field image, second 3D information regarding the area of interest is generated with a second algorithm different from the first algorithm.

19 Claims, 10 Drawing Sheets

(56) References Cited

U.S. PATENT DOCUMENTS

| | | | |
|---|---|---|---|
| 2008/0033291 A1* | 2/2008 | Rousso | A61B 5/416 600/436 |
| 2011/0085718 A1* | 4/2011 | Ingerman | G01N 23/046 382/131 |
| 2013/0009980 A1* | 1/2013 | Gu | G06T 5/00 345/643 |
| 2013/0208964 A1* | 8/2013 | Dwivedi | G06T 7/10 382/128 |
| 2014/0193336 A1* | 7/2014 | Rousso | A61B 6/503 600/431 |
| 2015/0078642 A1* | 3/2015 | Fang | G06T 7/0012 382/131 |
| 2015/0320514 A1* | 11/2015 | Ahn | A61B 34/30 606/130 |
| 2018/0160102 A1* | 6/2018 | Luo | G06T 7/55 |
| 2018/0214006 A1* | 8/2018 | Akimoto | A61B 1/00194 |
| 2020/0043189 A1* | 2/2020 | Bao | G06T 7/75 |
| 2020/0380711 A1* | 12/2020 | Luo | G06T 7/344 |
| 2021/0015343 A1* | 1/2021 | Uyama | A61B 1/0005 |
| 2021/0110574 A1* | 4/2021 | Kaino | G06T 7/521 |
| 2021/0142559 A1* | 5/2021 | Yousefhussien | G06Q 10/06315 |

FOREIGN PATENT DOCUMENTS

| | | |
|---|---|---|
| CN | 108135453 A | 6/2018 |
| EP | 2942029 A1 | 11/2015 |
| EP | 3330924 A1 | 6/2018 |
| JP | 2004113802 A | 4/2004 |
| JP | 2010521272 A | 6/2010 |
| JP | 2015-213753 A | 12/2015 |
| JP | 2018-124984 A | 8/2018 |
| KR | 10-2015-0128049 A | 11/2015 |
| KR | 10-2018-0062959 A | 6/2018 |
| WO | 2016/098665 A1 | 6/2016 |
| WO | 2017/057330 A1 | 4/2017 |
| WO | 2018-216342 A1 | 11/2018 |

OTHER PUBLICATIONS

Furukawa, et al., "Multi-View Stereo: A Tutorial", Foundations and Trends in Computer Graphics and Vision, vol. 9, No. 1-2, 2013, pp. 164.

Schoning, et al., "Evaluation of multi-view 3D reconstruction software", Computer Analysis of Images and Patterns (CAIP), Aug. 26, 2015, pp. 450-461.

* cited by examiner

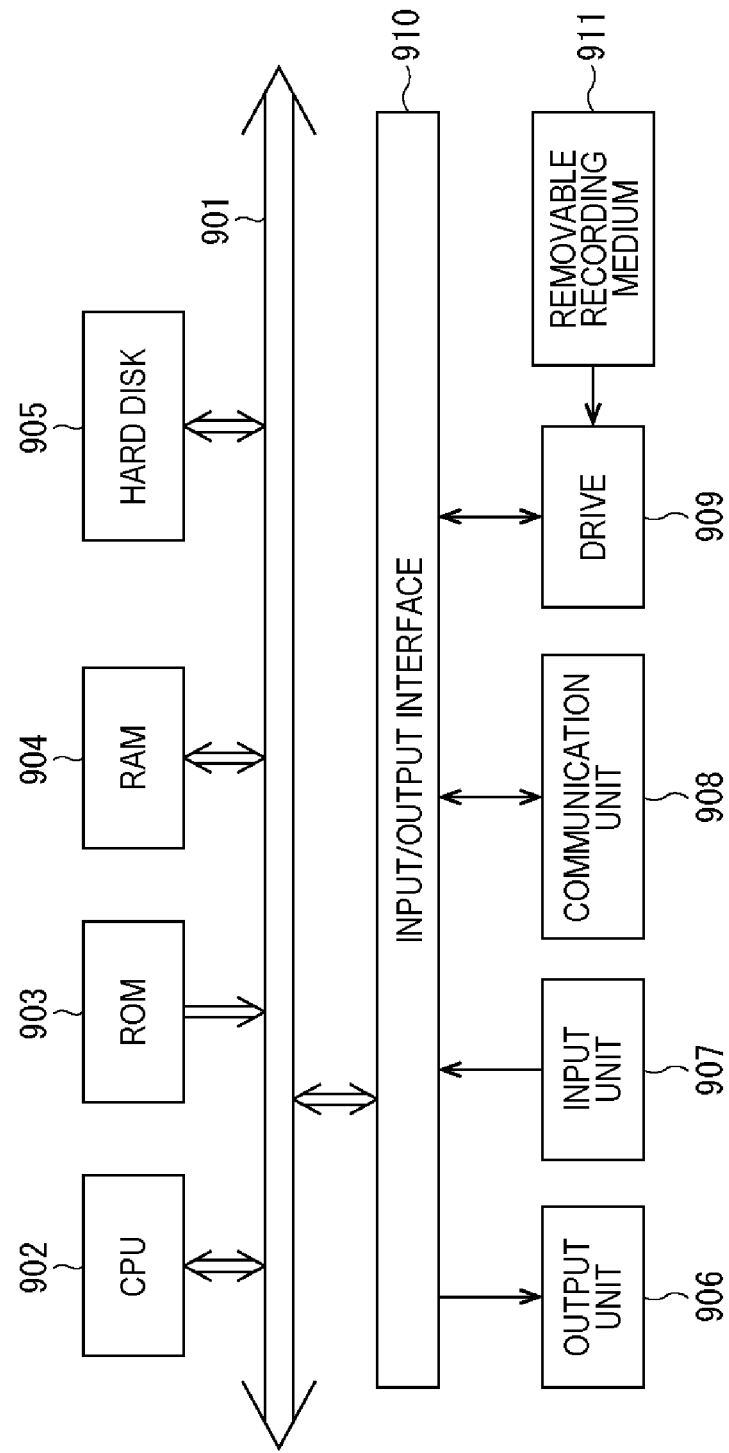

MEDICAL SYSTEM, SIGNAL PROCESSING DEVICE, AND SIGNAL PROCESSING METHOD

CROSS REFERENCE TO RELATED APPLICATIONS

This application is a U.S. National Phase of International Patent Application No. PCT/JP2020/010741 filed on Mar. 12, 2020, which claims priority benefit of Japanese Patent Application No. JP 2019-056683 filed in the Japan Patent Office on Mar. 25, 2019. Each of the above-referenced applications is hereby incorporated herein by reference in its entirety.

TECHNICAL FIELD

The present technology relates to a medical system, a signal processing device, and a signal processing method, and more particularly relates to, for example, a medical system, a signal processing device, and a signal processing method capable of obtaining highly accurate three-dimensional (3D) information in real time by using an operative field image obtained by imaging an operative field.

BACKGROUND ART

Regarding a medical system that performs an operation or the like by using an endoscope or a microscope, a technology for improving efficiency of the operation by using 3D information is proposed (see, for example, Patent Document 1).

CITATION LIST

Patent Document

Patent Document 1: WO 2016/098665 A

SUMMARY OF THE INVENTION

Problems to be Solved by the Invention

In a medical system using an endoscope or a microscope, an organ appearing in an operative field image obtained by imaging an operative field has fine unevenness such as blood vessels. In an operation, such fine unevenness is important in some cases.

However, an algorithm that generates 3D information for expressing fine unevenness with high accuracy and high density requires a large amount of calculation. This makes it difficult to always generate 3D information in real time.

The present technology has been made in view of such a situation, and makes it possible to obtain highly accurate 3D information in real time by using an operative field image.

Solutions to Problems

A medical system of the present technology is a medical system including: an imaging unit that images an operative field and outputs an operative field image; a first generation unit that generates 3D information regarding the operative field with a first algorithm by using the operative field image; and a second generation unit that, in a case where an area of interest is set in the operative field image, generates 3D information regarding the area of interest with a second algorithm different from the first algorithm.

A signal processing device according to the present technology is a signal processing device including: a first generation unit that generates 3D information regarding an operative field with a first algorithm by using an operative field image obtained by imaging the operative field; and a second generation unit that, in a case where an area of interest is set in the operative field image, generates 3D information regarding the area of interest with a second algorithm different from the first algorithm.

A signal processing method of the present technology is a signal processing method including: generating 3D information regarding an operative field with a first algorithm by using an operative field image obtained by imaging the operative field; and, in a case where an area of interest is set in the operative field image, generating 3D information regarding the area of interest with a second algorithm different from the first algorithm.

In the present technology, 3D information regarding an operative field is generated with the first algorithm by using an operative field image obtained by imaging the operative field. In a case where an area of interest is set in the operative field image, 3D information regarding the area of interest is generated with the second algorithm different from the first algorithm.

Note that each signal processing device may be an independent device, or may be an internal block forming a single device.

Further, the signal processing device can be achieved by causing a computer to execute a program. The program can be distributed by being recorded on a recording medium or being transmitted via a transmission medium.

BRIEF DESCRIPTION OF DRAWINGS

FIG. 10 is a block diagram illustrating a configuration example of an embodiment of a computer to which the present technology is applied.

MODE FOR CARRYING OUT THE INVENTION

<Embodiment of Medical System to which Present Technology is Applied>

Figure 1:
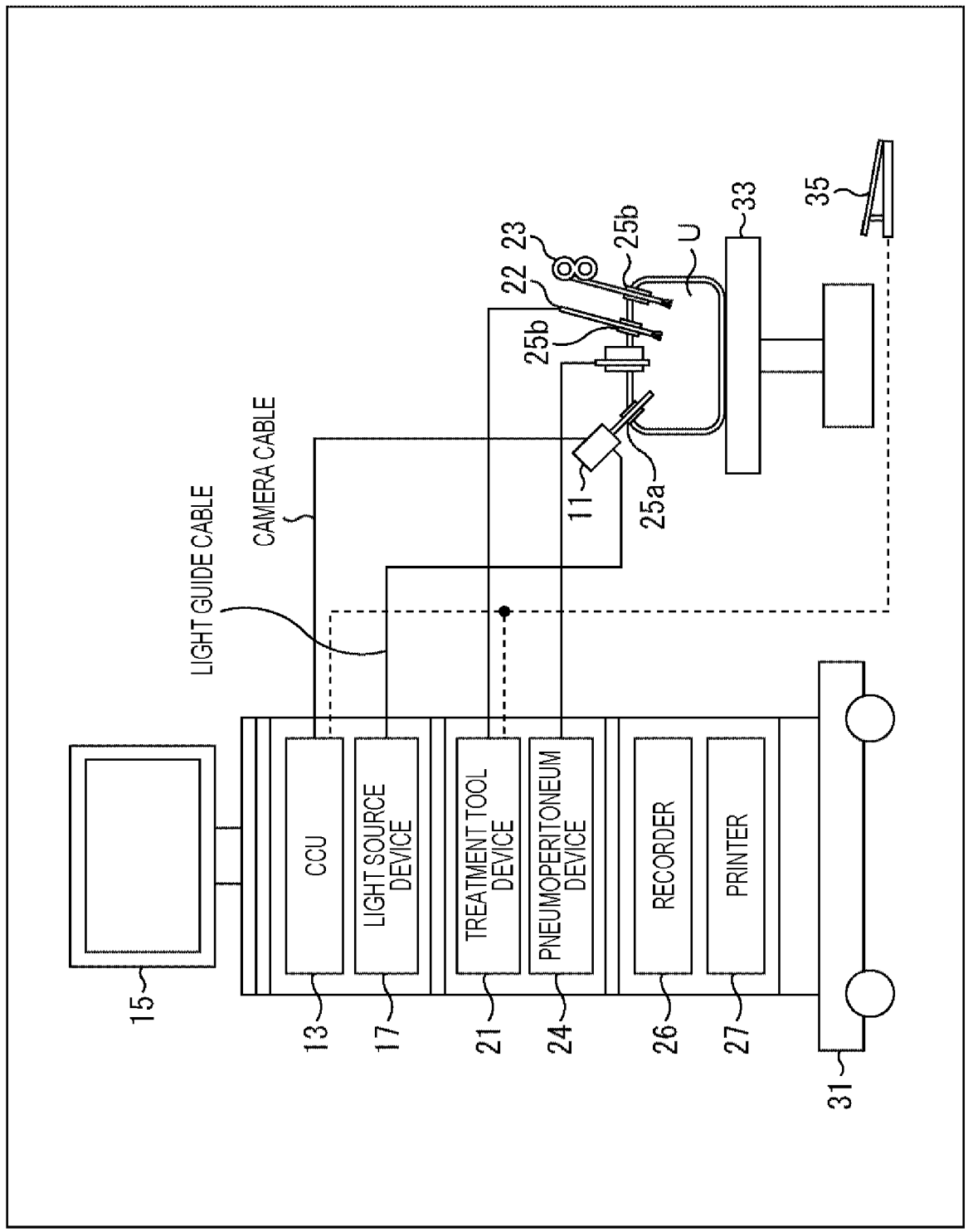
FIG. 1 is a block diagram illustrating a configuration example of an embodiment of a medical system to which the present technology is applied.

FIG. 1 is a block diagram illustrating a configuration example of an embodiment of a medical system to which the present technology is applied.

The medical system of FIG. 1 shows, for example, a configuration example of an endoscopic surgery system used for abdominal endoscopic surgery. Note that the present technology is applied not only to the endoscopic surgery system but also to a medical system using a microscope.

In the medical system of FIG. 1, trocars 25a and 25b serving as opening tools are inserted into several places of an abdominal wall in the abdominal endoscopic surgery or the like, without cutting the abdominal wall to open the abdomen. Then, a laparoscope (hereinafter, also referred to as an endoscope) 11 serving as an observation medical instrument for observing an inside of a body of a patient U, an energy treatment tool 22, forceps 23, and the like are inserted into the body through holes provided by the trocars 25a and 25b.

An operator performs treatment such as resecting, by using the energy treatment tool 22 and the like, an affected part (tumor or the like) in the body of the patient U imaged (as a video) by the endoscope 11 while viewing an image (moving image) of the affected part in real time. The endoscope 11, the energy treatment tool 22, and the forceps 23 are held by the operator, a robot, or the like. Note that the operator refers to a medical worker involved in an operation performed in an operating room, and examples of the operator include a surgeon, an assistant, a scopist, a nurse, and a doctor monitoring the operation from a place different from the operating room.

In the operating room in which such endoscopic surgery is performed, a cart 31 on which devices for the endoscopic surgery are mounted, a patient bed 33 on which the patient U lies, a foot switch 35, and the like are arranged. For example, devices such as a camera control unit (CCU) 13, a display device 15, a light source device 17, a treatment tool device 21, a pneumoperitoneum device 24, a recorder 26, and a printer 27 are placed as medical instruments on the cart 31.

The endoscope 11 includes a scope and a camera head. The scope is an optical system that guides light from an operative field illuminated by the light source device 17 to the camera head. The camera head is an imaging unit including an optical system, an image sensor, and the like. The endoscope 11 is inserted into the body of the patient U and captures an image (signal) inside the body of the patient U. The image of the affected part captured by the endoscope 11 is transmitted to the CCU 13 via a camera cable connected to the camera head. The CCU 13 may be connected to the endoscope 11 not only via the camera cable but also via a wireless communication path. The CCU 13 performs signal processing on the image output (transmitted) from the endoscope 11, and outputs the image subjected to the signal processing to the display device 15. With such a configuration, an operative field image showing the affected part is displayed on the display device 15. Note that the scope may be rigid or flexible.

Note that the CCU 13 may output the image subjected to the signal processing to the recorder 26 so as to cause the recorder 26 to record the operative field image. Further, the CCU 13 may output the image subjected to the signal processing to the printer 27 so as to cause the printer 27 to print the operative field image.

The light source device 17 generates light of various wavelengths. The light source device 17 is connected to the endoscope 11 via a light guide cable, and light generated by the light source device 17 is emitted toward the affected part through the endoscope 11. The light generated by the light source device 17 may be used as auxiliary light, for example.

The treatment tool device 21 is, for example, a high frequency output device that outputs a high frequency current to the energy treatment tool 22 that cuts the affected part by using electric heat.

The pneumoperitoneum device 24 includes air supply and air suction means, and supplies air to, for example, an abdominal area in the body of the patient U.

The foot switch 35 outputs a predetermined trigger signal to the CCU 13, the treatment tool device 21, and the like in response to a foot operation of the operator.

<Outline of SLAM>

Figure 2:
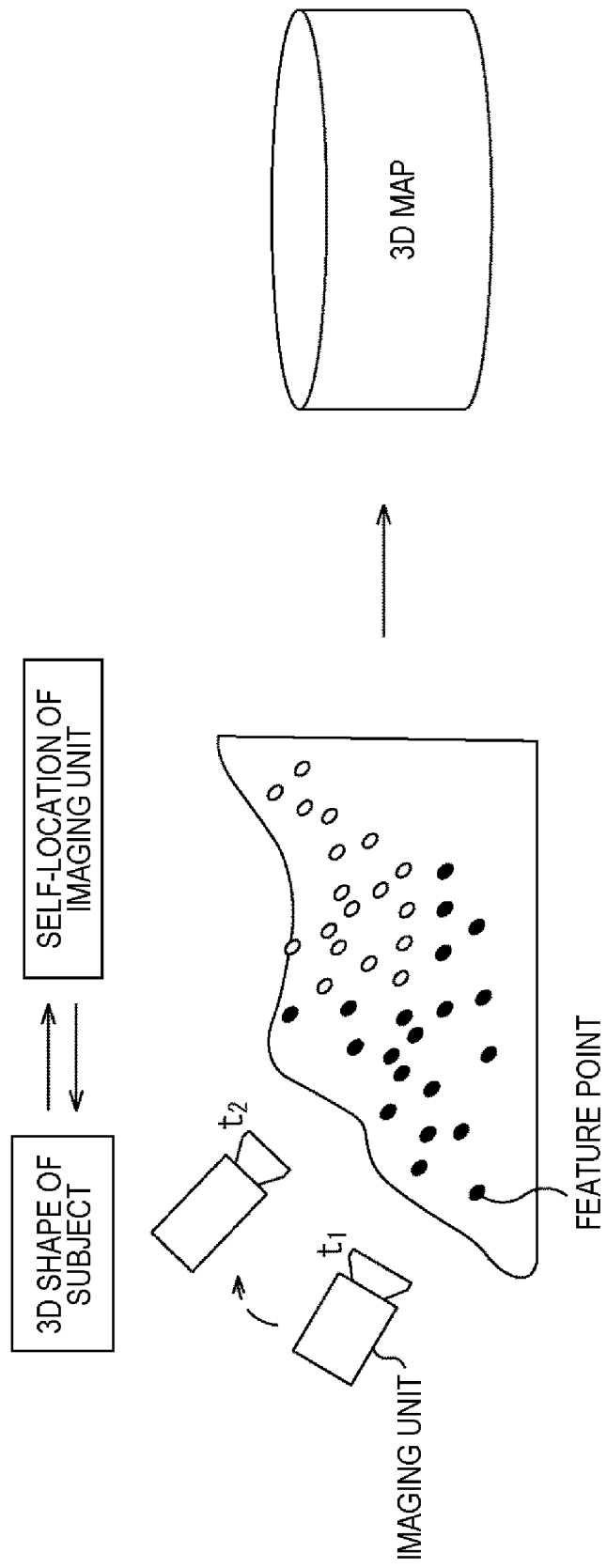
FIG. 2 illustrates an outline of SLAM.

FIG. 2 illustrates an outline of SLAM.

SLAM is a technology of generating a 3D map of a surrounding environment on the basis of only an image supplied from the imaging unit or on the basis of the image and sensor information other than the image and estimating a self-location (and posture) based on the imaging unit in the 3D map in real time.

The medical system of FIG. 1 can perform operation support by acquiring, with the SLAM, a 3D map for (a range to be) the operative field including an operative site (affected part) and a location of the endoscope 11 (e.g., a location of the imaging unit of the endoscope 11 or a location of a distal end of the scope of the endoscope 11) relative to the operative site. As the operation support, for example, an advising doctor gives an instruction to a surgeon regarding a part to be resected or the like on an operative field image by using a graphical user interface (GUI) during an operation, or navigates the operation by using the GUI while comparing the operative field image with a computed tomography (CT) image captured before the operation. Note that, in a case where the distal end of the scope of the endoscope 11 is set as a self-location, it is preferable to estimate a self-location of the imaging unit and then set the distal end of the scope as the self-location on the basis of information regarding the scope (e.g., information regarding a length from the imaging unit to the distal end of the scope and information regarding a shape of the scope). At this time, the information regarding the scope may be acquired by the CCU 13 as electrical information from the scope, or the CCU 13 may estimate the kind of scope from characteristics of the operative field image and read information associated with the scope estimated from information stored in advance. Further, a point at a preset distance from the imaging unit or a point on an optical axis of the endoscope 11 may be set as the self-location. In a case where the present medical system is applied to a microscope including an imaging unit, a relative location of the microscope (e.g., a distal end of the imaging unit of the microscope or a support supporting the imaging unit) is acquired.

In the SLAM, for example, feature points of an edge or the like are detected from an image captured by the moving imaging unit, and corresponding feature points appearing in images captured at different times t1 and t2 are associated as corresponding points. Further, in the SLAM, coordinates of the corresponding points in a 3D space are obtained, and a 3D shape of a subject and a 3D map of the 3D space captured by the imaging unit are generated as a set of points (point cloud) represented by coordinates of a large number of corresponding points in the 3D space. Furthermore, in the SLAM, the self-location of the imaging unit is estimated, for example, by solving a simultaneous equation based on the coordinates of the feature points.

The SLAM using an image captured by the imaging unit is referred to as Visual SLAM. The SLAM is disclosed in, for example, Andrew J. Davison, "Real-Time Simultaneous Localization and Mapping with a Single Camera", Proceedings of the 9th IEEE International Conference on Computer Vision Volume 2, 2003, pp. 1403-1410.

<Outline of Operation Support>

Figure 3:
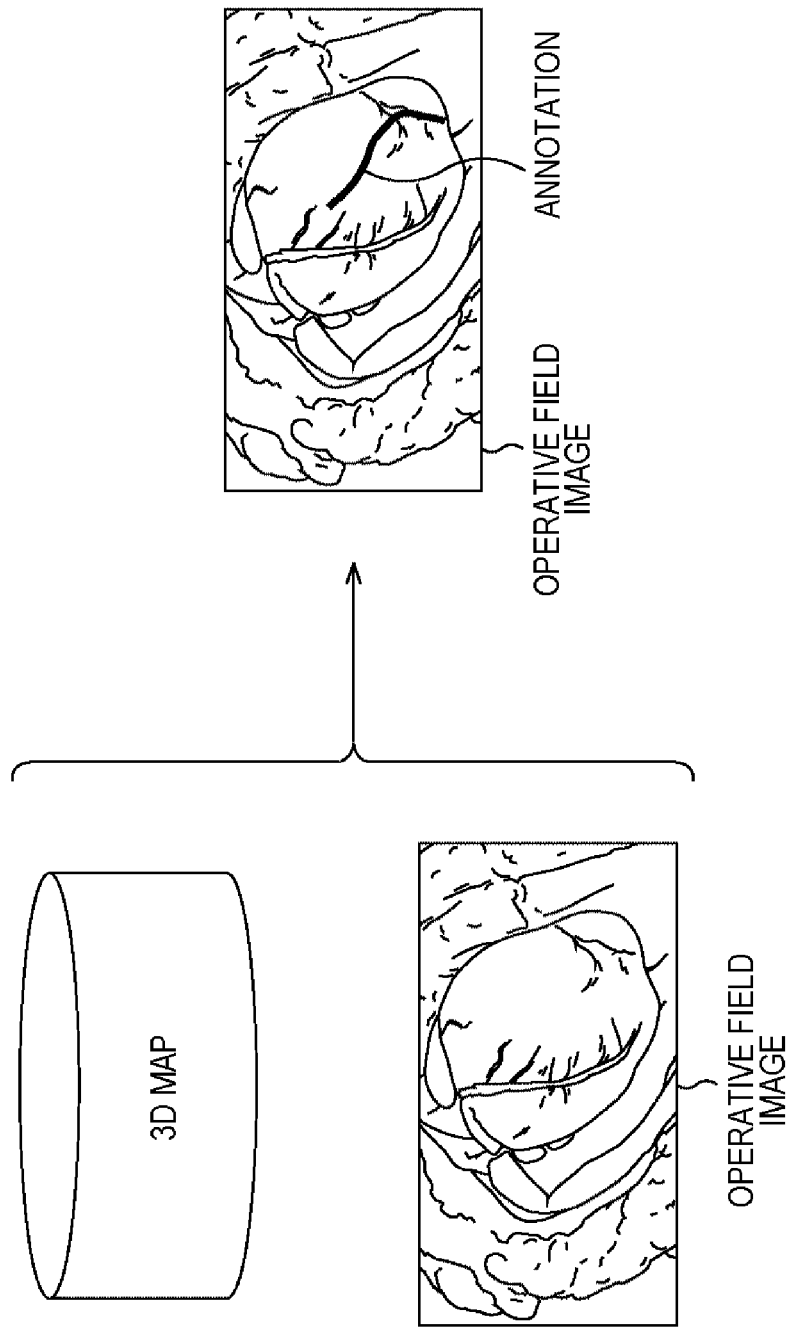
FIG. 3 illustrates an example of operation support using SLAM.

FIG. 3 illustrates an example of the operation support using the SLAM.

As the operation support, for example, in response to an operation from the advising doctor, the medical system of FIG. 1 can draw an annotation for specifying a part to be resected or the like to instruct the surgeon at a location on the operative field image specified by the advising doctor.

Further, even in a case where the location and posture of the endoscope 11 change, the medical system of FIG. 1 can display the annotation while following the location on the operative field image specified by the advising doctor in accordance with the 3D map and the self-location based on the imaging unit obtained by the SLAM.

<First Configuration Example of Endoscope 11 and CCU 13>

Figure 4:
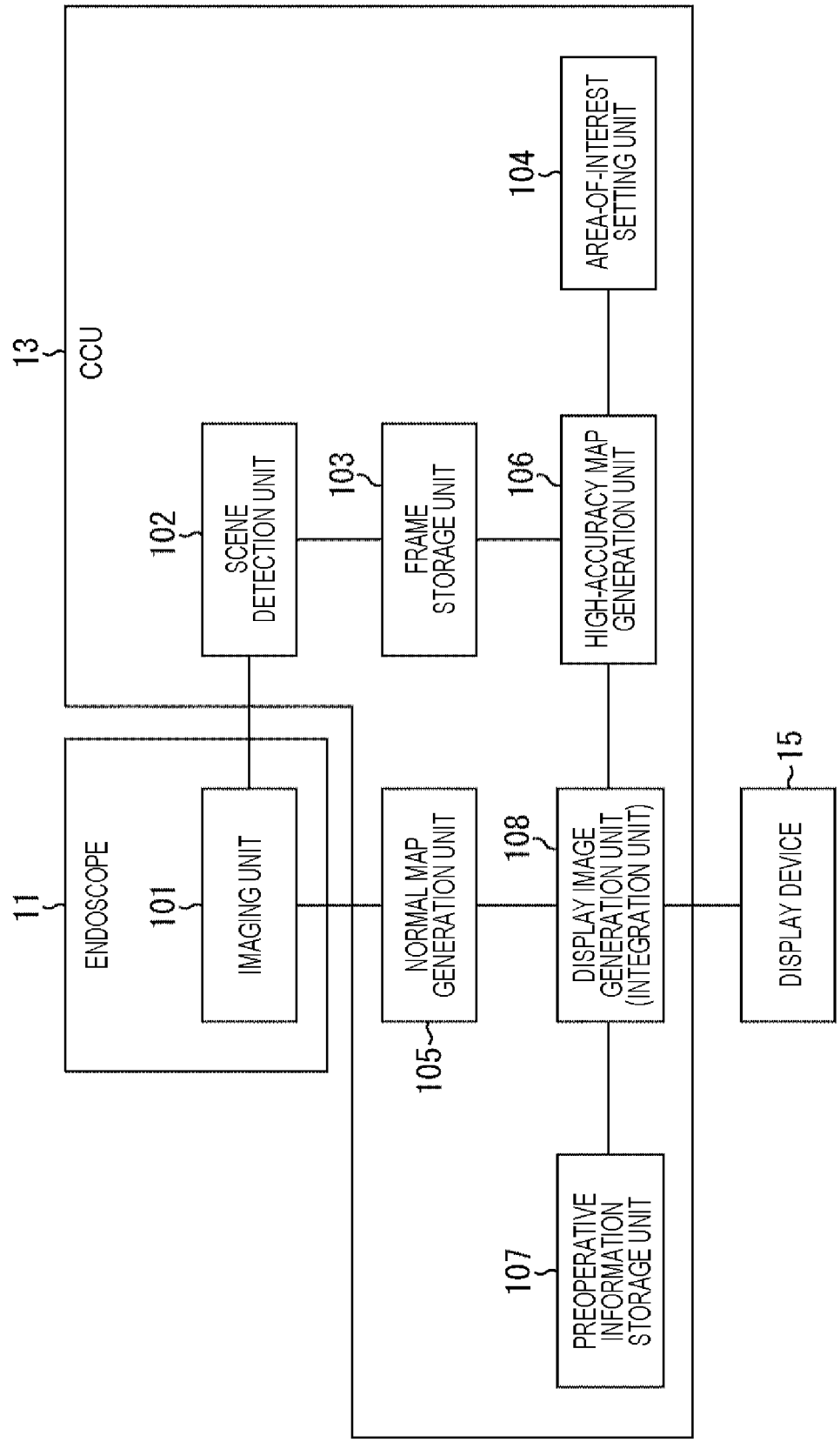
FIG. 4 is a block diagram illustrating a first configuration example of an endoscope 11 and a CCU 13.

FIG. 4 is a block diagram illustrating a first configuration example of the endoscope 11 and the CCU 13 of FIG. 1.

Herein, in the medical system, for example, the 3D map used in an application such as for drawing an annotation as described with reference to FIG. 3 is desirably highly accurate in terms of safety.

However, the SLAM such as the Visual SLAM described above is excellent in a real-time property, but has a sparse point cloud on the 3D map and includes many outliers.

Meanwhile, an algorithm (calculation model) that generates a dense (point cloud) and highly accurate 3D map by using multi-view images is, for example, Structure from Motion (SfM) such as Multi-view stereo. The Multi-view stereo is disclosed in, for example, Multi-View Stereo: A Tutorial. Foundations and. TrendsR in Computer Graphics and Vision, vol. 9, no. 1-2, 2013, pp. 1-148, and Evaluation of multi-view 3D reconstruction software, CAIP 2015: Computer Analysis of Images and Patterns, pp. 450-461.

According to the Multi-view stereo, a dense and highly accurate 3D map can be generated. However, the Multi-view stereo requires a high calculation load and a long processing time and is therefore not suitable for uses requiring localization and generation (update) of a 3D map in real time.

In view of this, the CCU 13 performs generation of a 3D map (3D information) for an operative field and localization in real time with, for example, the Visual SLAM serving as a first algorithm by using an operative field image obtained by the endoscope 11 capturing an image of (a range to be) the operative field. Further, in a case where an area of interest is set in the operative field image, the CCU 13 generates a 3D map for the area of interest with, for example, the Multi-view stereo serving as a second algorithm different from the first algorithm. Therefore, it is possible to provide a dense and highly accurate 3D map for the area of interest, for example, an area required by the operator, while ensuring the real-time property for generating the 3D map and performing localization. That is, it is possible to achieve both the real-time property and high accuracy of the 3D map.

In FIG. 4, the endoscope 11 includes an imaging unit 101, and the CCU 13 includes a scene detection unit 102, a frame storage unit 103, an area-of-interest setting unit 104, a normal map generation unit 105, a high-accuracy map generation unit 106, a preoperative information storage unit 107, and a display image generation unit 108.

For example, the imaging unit 101 receives visible rays of light of an operative field to thereby image the operative field, and outputs an RGB (Red, Green, Blue) image obtained by the imaging as an operative field image. The operative field image output by the imaging unit 101 is supplied to the scene detection unit 102 and the normal map generation unit 105. Further, the operative field image output by the imaging unit 101 is supplied to the display image generation unit 108 via the normal map generation unit 105.

The scene detection unit 102 detects, for example, an obstructive scene that obstructs generation of a 3D map as a specific scene from each frame of the operative field image supplied from the imaging unit 101. Examples of the obstructive scene include bleeding, smoking, and overexposure.

In a case where the obstructive scene is detected, the scene detection unit 102 restricts output of a frame of the operative field image showing the obstructive scene to the frame storage unit 103. Therefore, the frame of the operative field image showing the obstructive scene is not output from the scene detection unit 102 to the frame storage unit 103.

Meanwhile, in a case where no obstructive scene is detected, the scene detection unit 102 outputs the frames of the operative field image to the frame storage unit 103.

Herein, a method of detecting a bleeding scene as the obstructive scene is, for example, to identify a bleeding area only from an image by using an image recognition technology or the like.

A method of detecting a smoking scene as the obstructive scene is, for example, to detect a cauterization scene by using the image recognition technology or the like.

A method of detecting an overexposure scene as the obstructive scene is, for example, to detect a scene in which overexposure occurs or tends to occur by using the image recognition technology or the like.

The frame storage unit 103 selects a frame to be used for generating a high-accuracy map as a key frame from the frames of the operative field image output by the scene detection unit 102 and stores the frame.

In FIG. 4, the scene detection unit 102 does not output the frame of the operative field image showing the obstructive scene to the frame storage unit 103. Therefore, the frame storage unit 103 stores, as a key frame, a frame selected from the frames of the operative field image output by the imaging unit 101 other than the frame (specific frame) showing the obstructive scene, that is, the frames of the operative field image not showing the obstructive scene.

Herein, in FIG. 4, as described later, the high-accuracy map generation unit 106 generates a high-accuracy map that is a highly accurate (and dense) 3D map by using the key frame of the operative field image stored in the frame storage unit 103 with, for example, SfM such as the Multi-view stereo serving as the second algorithm.

In order to efficiently generate a high-accuracy map in the high-accuracy map generation unit 106 with the Multi-view stereo, it is desirable that images (frames) from more different viewpoints exist as key frames.

Therefore, the frame storage unit 103 detects a change in a viewpoint (location) of the imaging unit 101 on the basis of a track of the imaging unit 101 of the endoscope 11 that is localized by the normal map generation unit 105 and a change in the number of feature points in the operative field. Then, the frame storage unit 103 switches, for example, the way to select and store the key frame, such as an interval of selecting the key frame, from the frames of the operative field image output by the scene detection unit 102 in accordance with the change in the viewpoint of the imaging unit 101.

For example, the frame storage unit 103 performs threshold processing on an amount of change in the viewpoint of the imaging unit 101, thereby determining whether or not the viewpoint of the imaging unit 101 is in a steady state (substantially stopped) or in a moving state.

In a case where the viewpoint of the imaging unit 101 is in the steady state, a scene appearing in the frames of the operative field image output by the scene detection unit 102 hardly changes. Therefore, the frame storage unit 103 selects the latest frame output by the scene detection unit 102 as a key frame, and stores the key frame by overwriting a frame previously stored as a key frame, for example, a frame stored as a key frame immediately before the latest frame.

Further, in a case where the viewpoint of the imaging unit 101 is in the moving state, (the range to be) the operative field changes. Thus, new feature points are detected in the Visual SLAM performed by the normal map generation unit 105. Therefore, every time a predetermined number of new feature points are detected, the frame storage unit 103 selects and stores a frame output by the scene detection unit 102 as a key frame.

As described above, the frame storage unit 103 can switch a frequency of selecting the key frame according to the change in the viewpoint of the imaging unit 101.

Note that the maximum number of frames stored as key frames in the frame storage unit 103 can be determined in advance. In a case where the maximum number of key frames is stored in the frame storage unit 103, the oldest key frame is overwritten to store a new key frame.

The area-of-interest setting unit 104 sets an area of interest in (a frame of) the operative field image. Regarding the operative field image, a partial area of the frame of the operative field image can be set as the area of interest, or the entire area of the frame of the operative field image can be set as the area of interest.

Herein, the high-accuracy map generation unit 106 generates a high-accuracy map for the area of interest with the Multi-view stereo. According to the Multi-view stereo, it is possible to generate a high-accuracy map that is a highly accurate (and dense) 3D map. However, the Multi-view stereo requires a high calculation load and a long processing time and therefore obstructs the real-time property in a case where the entire frame is set as a target of the Multi-view stereo. Further, in order to ensure the real-time property while generating a high-accuracy map for the entire frame with the Multi-view stereo, an extremely high-speed device is required as the CCU 13. This increases a cost of the medical system.

In view of this, the area-of-interest setting unit 104 can set, as the area of interest, a partial area of the operative field image within a size that does not reduce the real-time property even in a case where the Multi-view stereo is executed for a long time. Further, the area-of-interest setting unit 104 can set, as the area of interest, the entire area of the frame of the operative field image within a range of a short time (e.g., several seconds or the like) that does not reduce the real-time property even in a case where the entire area of the frame of the operative field image is set as a target of the Multi-view stereo.

For example, the area-of-interest setting unit 104 can set, in the operative field image, only (an area showing) an operative site to be operated on as the area of interest. Further, for example, the area-of-interest setting unit 104 can set the entire area of the frame of the operative field image as the area of interest in a short (e.g., several seconds) scene in which an organ is cut out by using an electric scalpel serving as the energy treatment tool 22.

The area-of-interest setting unit 104 can set, as the area of interest, an area requiring high accuracy or an area estimated to require high accuracy in the operative field image.

The area of interest can be set, for example, in response to specification from the operator. For example, the operator can set, in the operative field image displayed on the display device 15, an area surrounded by operating a user interface (UI) as the area of interest. Further, for example, it is possible to divide the operative field image displayed on the display device 15 into a plurality of divided areas in advance, and, in response to voice of a user (e.g., "upper right", "lower left", and the like) to specify a divided area, set the divided area specified by the voice as the area of interest. Furthermore, for example, it is possible to detect a line of sight of the operator viewing the operative field image displayed on the display device 15, and set, as the area of interest, an area including a location viewed by the operator which is estimated from the line of sight.

The area of interest can be set according to, for example, information obtained before an operation or information obtained during the operation. For example, it is possible to recognize an object specified in advance with object recognition or the like using the information obtained before the operation or the information obtained during the operation, and set the area of interest by using a recognition result of the object.

For example, it is possible to specify a lesion site or a site to be operated on in advance in a medical image such as a CT image, and set an area having a shape matching with that of the site specified in advance (an area showing the site specified in advance) as the area of interest in a normal map obtained by the normal map generation unit 105 or a normal map into which a high-accuracy map is integrated, the normal map being obtained by the display image generation unit 108.

Further, for example, it is possible to predict an area to be highly accurate from a previous history with an artificial intelligence technology or the like, and set the area as the area of interest. Furthermore, for example, it is possible to perform learning for recognizing an operation instrument in advance by using an image of the operation instrument, recognize the operation instrument, and set, as the area of interest, an area showing a site where treatment is performed by using the operation instrument.

In addition, for example, the area of interest can be set in response to specification from a predetermined robot. For example, in a case where the endoscope 11 is supported by a scope holder robot and the scope holder robot has a function of specifying an area, an area specified by the scope holder robot can be set as the area of interest.

By using the operative field image output by the imaging unit 101, the normal map generation unit 105 generates a 3D map and performs localization for the entire range of the operative field image with the SLAM such as the Visual SLAM serving as the first algorithm.

In order to generate a 3D map and perform localization, it is possible to employ, as the first algorithm, not only the Visual-SLAM using only an image but also a 3D map generation algorithm capable of ensuring the real-time property regardless of a degree of accuracy (and density) of a point cloud forming a 3D map.

Note that it is possible to employ, as the first algorithm, an algorithm that only generates a 3D map without performing localization. However, in a case where the algorithm that only generates a 3D map is employed as the first algorithm, localization needs to be separately performed.

Further, it is possible to employ, as the first algorithm, not only the algorithm that generates a 3D map (3D information) by using only an image but also an algorithm that generates a 3D map by using an image and depth information output by a ToF sensor, Lidar, or the like.

Herein, the 3D map generated in real time by the normal map generation unit 105 with the first algorithm is also referred to as a normal map. The normal map is a 3D map for recognizing a relative positional relationship with the self-location based on the imaging unit 101 in the 3D space imaged by the imaging unit 101.

In a case where the area-of-interest setting unit 104 sets the area of interest, the high-accuracy map generation unit 106 generates a 3D map for the area of interest serving as a target area, that is, recognizes a 3D shape of an object appearing in the area of interest, by using the key frame of the operative field image stored in the frame storage unit 103 with, for example, SfM such as the Multi-view stereo serving as the second algorithm.

As the second algorithm, it is possible to employ a 3D map generation algorithm capable of generating a 3D map having higher accuracy than the normal map. Because the 3D map generated by the second algorithm is more highly accurate than the normal map generated by the first algorithm, the second algorithm requires a high calculation load and a long processing time. Conversely, an algorithm requiring a smaller amount of calculation than the second algorithm is employed as the first algorithm so as to ensure the real-time property.

Further, the first algorithm is used to generate a normal map for the entire range (operative field) of the operative field image, whereas the second algorithm is used to generate a 3D map only for the area of interest.

Note that it is possible to employ, as the second algorithm, an algorithm that does not perform localization. However, the second algorithm may be an algorithm that performs localization.

Herein, the 3D map having higher accuracy than the normal map, which is generated by the high-accuracy map generation unit 106 with the second algorithm, is also referred to as a high-accuracy map. The high-accuracy map expresses a 3D shape of the area of interest with higher accuracy than the normal map. In the Visual SLAM serving as the first algorithm, it is possible to generate a 3D map (normal map) at a high frame rate, although accuracy thereof is reduced as compared with the second algorithm. Meanwhile, in the Multi-view stereo serving as the second algorithm, it is difficult to generate a 3D map (high-accuracy map) at a high frame rate, but it is possible to generate a highly accurate 3D map.

The preoperative information storage unit 107 stores preoperative information obtained before an operation. The preoperative information is, for example, a 3D model constructed from a CT image captured before the operation.

The display image generation unit 108 functions as an integration unit that integrates a (dense) high-accuracy map generated by the high-accuracy map generation unit 106 into a (sparse) normal map generated by the normal map generation unit 105.

That is, the display image generation unit 108 functioning as the integration unit aligns the high-accuracy map (area of interest) with the normal map and integrates the aligned high-accuracy map into the normal map.

As a method of integrating the high-accuracy map into the normal map, a registration method such as iterative closest point (ICP) can be employed.

Herein, in a case where a new area of interest set by the area-of-interest setting unit 104 overlaps with a previous area of interest, the display image generation unit 108 deletes a high-accuracy map for the previous area of interest integrated into the normal map, and integrates a high-accuracy map for the new area of interest newly generated by the high-accuracy map generation unit 106 into the normal map from which the high-accuracy map for the previous area of interest has been deleted. This is because, in a case where the new area of interest overlaps with the previous area of interest, a shape of a part appearing in the area of interest may be different between the new area of interest and the previous area of interest due to, for example, cutting out an organ appearing in the area of interest or the like. This is performed to reflect a part appearing in the latest area of interest in the normal map.

The display image generation unit 108 generates a display image to be displayed on the display device 15 by using not only the operative field image output by the imaging unit 101 but also the normal map into which the high-accuracy map is integrated and the preoperative information stored in the preoperative information storage unit 107 as necessary, thereby supplying the display image to the display device 15.

For example, the display image generation unit 108 can specify, by using the normal map, a location in the 3D space where the operator has given an instruction to display an annotation, and generate, as a display image, an operative field image in which the annotation is drawn at the location.

<Signal Processing Performed by CCU 13>

Figure 5:
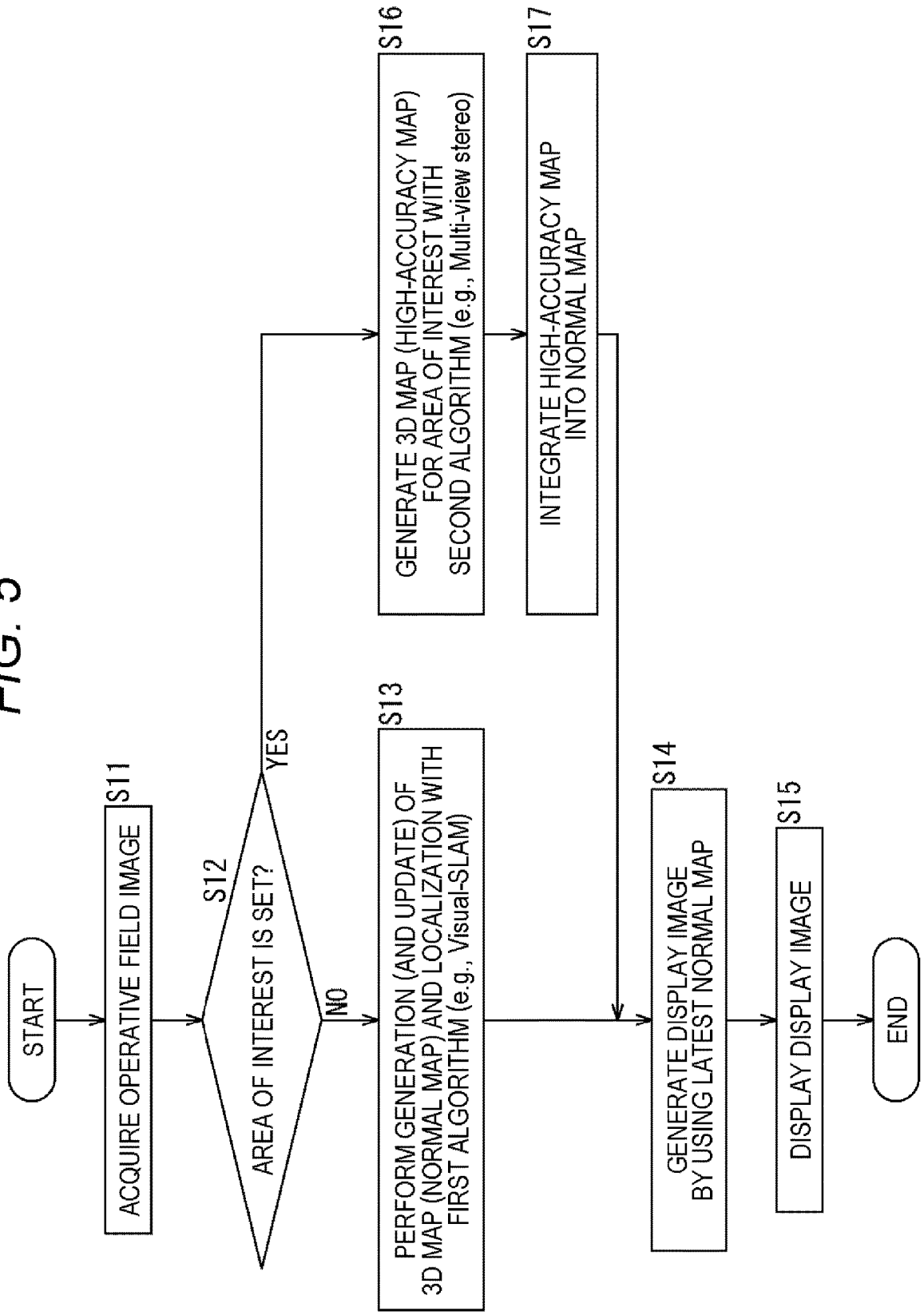
FIG. 5 is a flowchart showing a first example where the CCU 13 generates a normal map and a high-accuracy map.

FIG. 5 is a flowchart showing a first example where the CCU 13 generates a normal map and a high-accuracy map.

In step S11, the CCU 13 acquires frames of an operative field image sequentially output by the imaging unit 101. The frames of the operative field image output by the imaging unit 101 are stored in the frame storage unit 103 as a key frame as necessary, and the processing proceeds from step S11 to step S12.

In step S12, in the CCU 13, the high-accuracy map generation unit 106 determines whether or not the area-of-interest setting unit 104 has set an area of interest.

In a case where it is determined in step S12 that the area of interest has not been set, the processing proceeds to step S13.

In step S13, the normal map generation unit 105 uses the frames of the operative field image output by the imaging unit 101 to perform generation (and update) of a normal map and localization of the imaging unit 101 with the Visual SLAM serving as the first algorithm, and the processing proceeds to step S14.

In step S14, the display image generation unit 108 generates a display image by using the latest normal map as necessary, and the processing proceeds to step S15.

In step S15, the display image generation unit 108 causes the display device 15 to display the display image.

Meanwhile, in a case where it is determined in step S12 that the area of interest has been set, the processing proceeds to step S16.

In step S16, the high-accuracy map generation unit 106 generates a high-accuracy map only for the area of interest with the Multi-view stereo serving as a second calculation algorithm, and the processing proceeds to step S17.

In step S17, the display image generation unit 108 integrates the latest high-accuracy map into the latest normal map. Then, the processing proceeds from step S17 to step S14, and the above-described processing is performed.

In the first example of generating a normal map and a high-accuracy map in FIG. 5, the normal map is generated in a case where the area of interest is not set, and the normal map is not generated and the high-accuracy map for only the area of interest is generated in a case where the area of interest is set.

Figure 6:
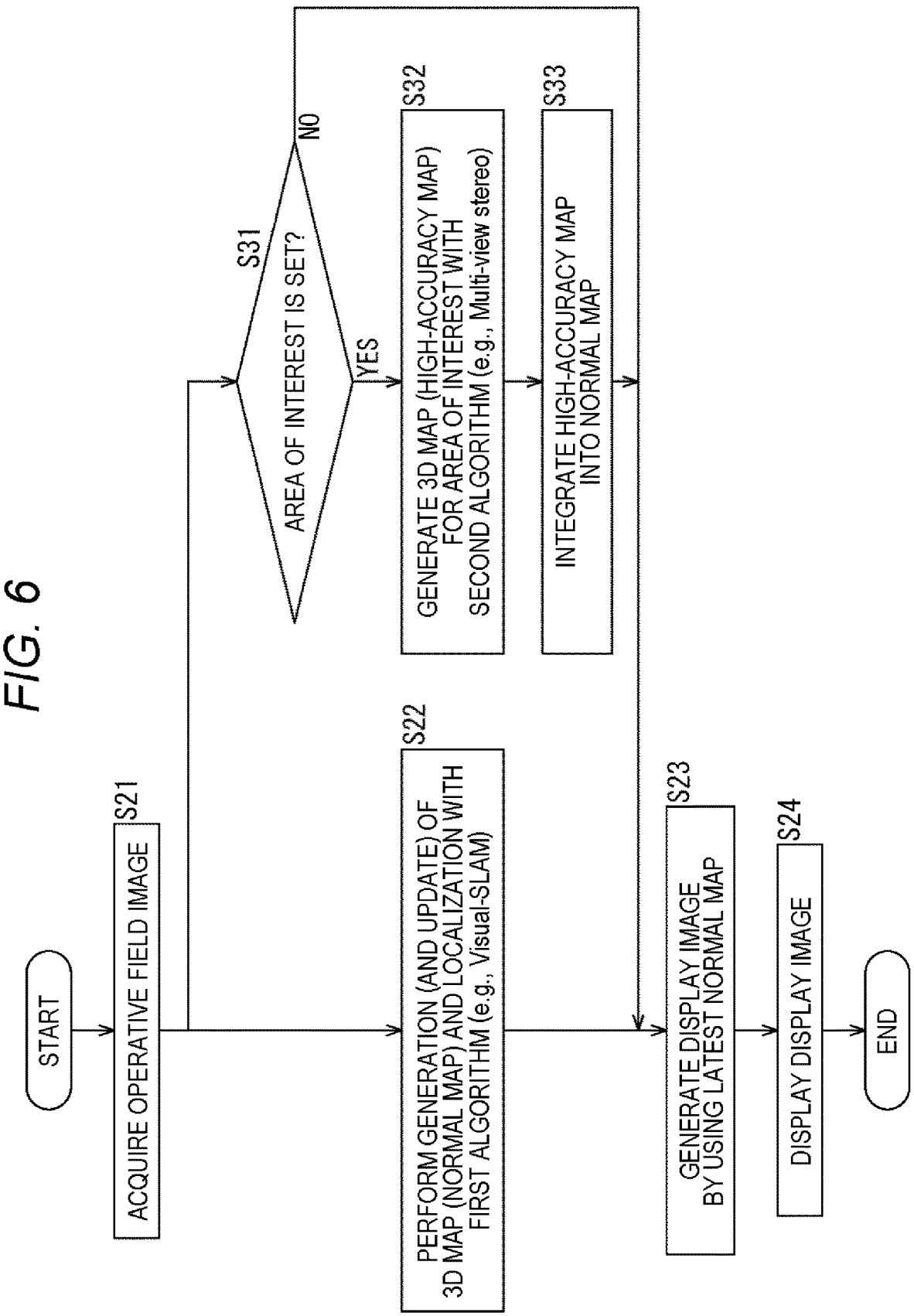
FIG. 6 is a flowchart showing a second example where the CCU 13 generates a normal map and a high-accuracy map.

FIG. 6 is a flowchart showing a second example where the CCU 13 generates a normal map and a high-accuracy map.

In step S21, as in step S11 of FIG. 5, the CCU 13 acquires frames of an operative field image output by the imaging unit 101 and stores the frames in the frame storage unit 103 as a key frame as necessary. Then, the processing proceeds from step S21 to step S22 and step S31 in parallel.

In step S22, as in step S13 of FIG. 5, the normal map generation unit 105 uses the frames of the operative field image output by the imaging unit 101 to perform generation of a normal map and localization of the imaging unit 101 with the Visual SLAM serving as the first algorithm, and the processing proceeds to step S23.

In step S23, as in step S14 of FIG. 5, the display image generation unit 108 generates a display image by using the latest normal map as necessary, and the processing proceeds to step S24.

In step S24, as in step S15 of FIG. 5, the display image generation unit 108 causes the display device 15 to display the display image.

Meanwhile, in step S31, as in step S12 of FIG. 5, in the CCU 13, the high-accuracy map generation unit 106 determines whether or not the area-of-interest setting unit 104 has set an area of interest.

In a case where it is determined in step S31 that the area of interest has not been set, the processing skips steps S32 and S33 and proceeds to step S23.

Meanwhile, in a case where it is determined in step S31 that the area of interest has been set, the processing proceeds to step S32.

In step S32, as in step S16 of FIG. 5, the high-accuracy map generation unit 106 generates a high-accuracy map only for the area of interest with the Multi-view stereo serving as the second calculation algorithm, and the processing proceeds to step S33.

In step S33, as in step S17 of FIG. 5, the display image generation unit 108 integrates the latest high-accuracy map into the latest normal map. Then, the processing proceeds from step S33 to step S23, and the above-described processing is performed.

In the second example of generating a normal map and a high-accuracy map in FIG. 6, the normal map is always generated regardless of whether or not the area of interest is set. As in FIG. 5, the high-accuracy map is generated only for the area of interest only in a case where the area of interest is set.

Figure 7:
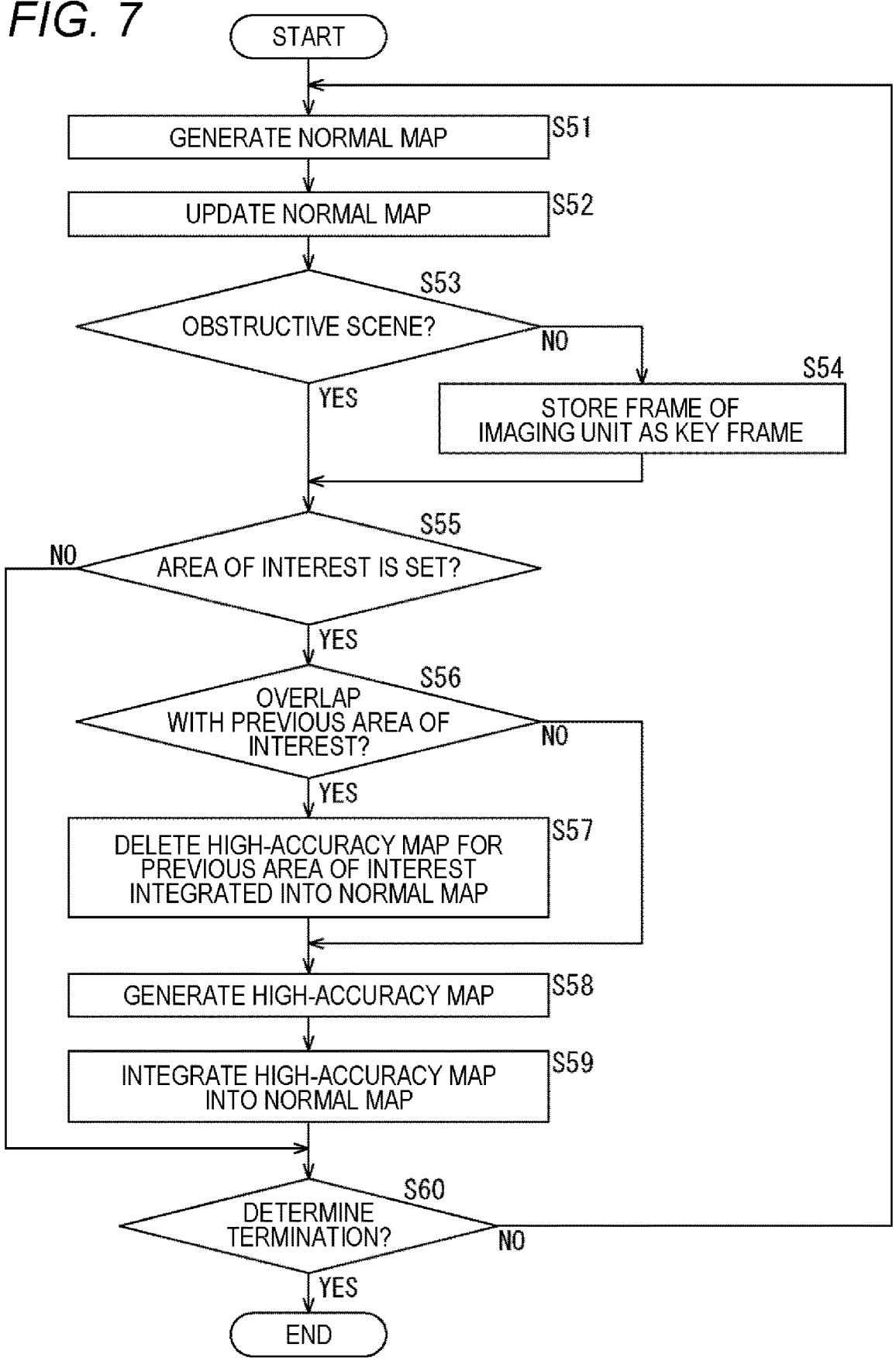
FIG. 7 is a flowchart showing an example of signal processing performed by the CCU 13.

FIG. 7 is a flowchart showing an example of signal processing performed by the CCU 13 of FIG. 4.

In step S51, the normal map generation unit 105 uses the operative field image output by the imaging unit 101 to perform generation of a normal map and localization in real time with the first algorithm having a smaller amount of calculation than the second algorithm, and the processing proceeds to step S52.

In step S52, the normal map generation unit 105 updates the normal map with the normal map generated in the preceding step S51, and the processing proceeds to step S53.

In step S53, the scene detection unit 102 determines whether or not the (latest) frame of the operative field image output by the imaging unit 101 is an obstructive frame showing an obstructive scene.

In a case where it is determined in step S53 that the frame of the operative field image output by the imaging unit 101 is not an obstructive frame, the processing proceeds to step S54.

In step S54, the frame storage unit 103 stores the frame of the operative field image that is not the obstructive frame as a key frame as necessary, and the processing proceeds to step S55.

Meanwhile, in a case where it is determined in step S53 that the frame of the operative field image output by the imaging unit 101 is an obstructive frame, the processing skips step S54 and proceeds to step S55. Therefore, the obstructive frame is not stored in the frame storage unit 103 herein.

In step S55, the high-accuracy map generation unit 106 determines whether or not the area-of-interest setting unit 104 has set an area of interest.

In a case where it is determined in step S55 that the area of interest has not been set, the processing skips steps S56 to S59 and proceeds to step S60.

Meanwhile, in a case where it is determined in step S55 that the area of interest has been set, the processing proceeds to step S56.

In step S56, the display image generation unit 108 determines whether or not (the entire or part of) the new area of interest determined to have been set in the preceding step S55 overlaps with the previous area of interest.

In a case where it is determined in step S56 that the new area of interest does not overlap with the previous area of interest, the processing skips step S57 and proceeds to step S58.

Meanwhile, in a case where it is determined in step S56 that the new area of interest overlaps with the previous area of interest, the processing proceeds to step S57.

In step S57, the display image generation unit 108 deletes a high-accuracy map for the previous area of interest integrated into the normal map, and the processing proceeds to step S58.

In step S58, the high-accuracy map generation unit 106 uses the key frame stored in the frame storage unit 103 to generate a high-accuracy map only for the new area of interest with the second algorithm having higher accuracy than the first algorithm, and the processing proceeds to step S59.

In step S59, the high-accuracy map is integrated into the normal map, and the processing proceeds to step S60.

In step S60, the CCU 13 determines whether to terminate the signal processing, and, in a case where it is determined not to terminate the signal processing, the processing returns to step S51, and the similar processing is repeated therefrom.

Meanwhile, in a case where it is determined in step S60 to terminate the signal processing, that is, for example, in a case where the operator operates the medical system to terminate the signal processing, the CCU 13 terminates the signal processing.

<Second Configuration Example of Endoscope 11 and CCU 13>

Figure 8:
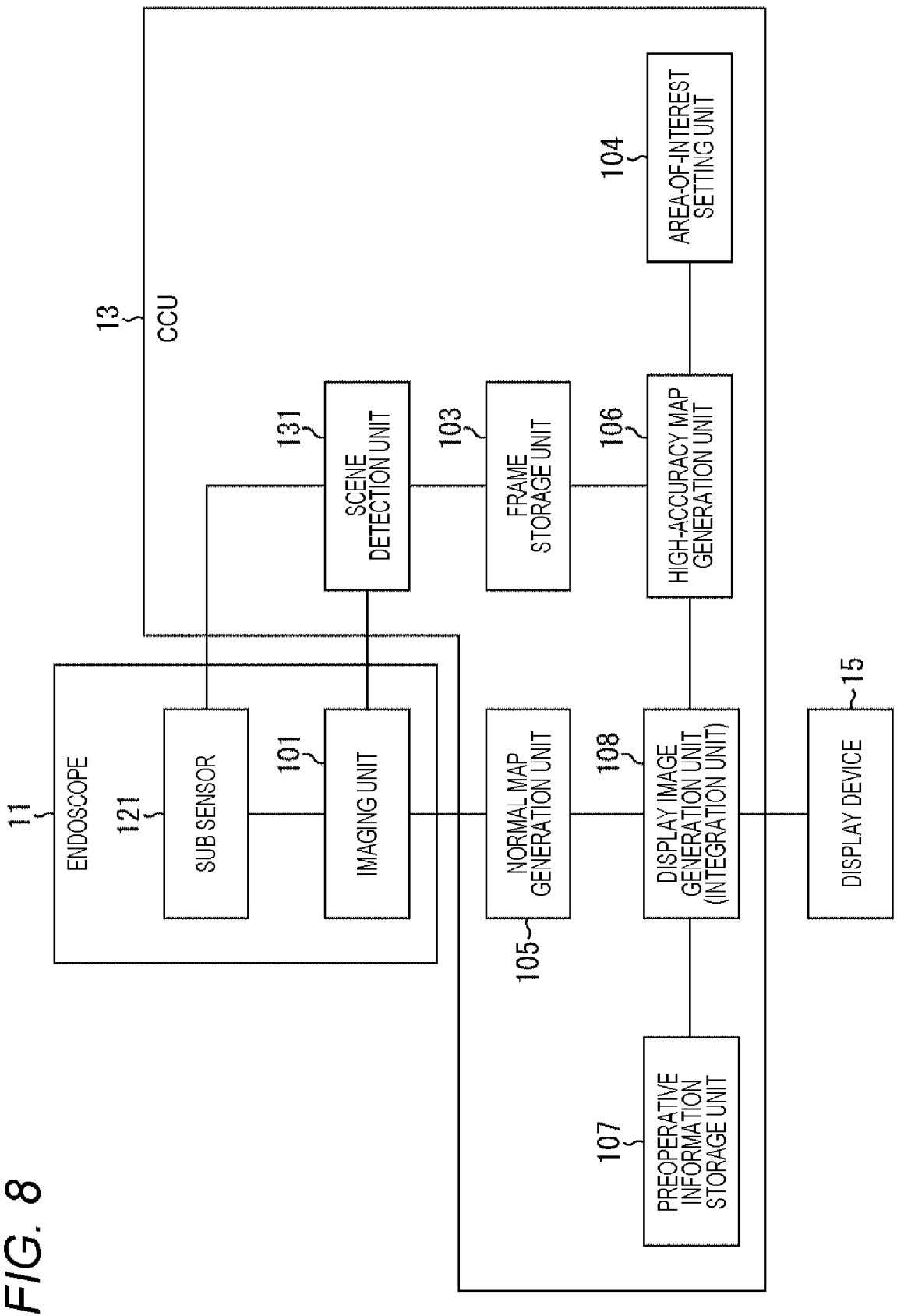
FIG. 8 is a block diagram illustrating a second configuration example of the endoscope 11 and the CCU 13.

FIG. 8 is a block diagram illustrating a second configuration example of the endoscope 11 and the CCU 13 of FIG. 1.

Note that parts in FIG. 8 corresponding to those in FIG. 4 are denoted by the same reference signs, and description thereof will be appropriately omitted below.

In FIG. 8, the endoscope 11 includes the imaging unit 101 and a sub sensor 121. Therefore, the endoscope 11 of FIG. 8 is the same as that of FIG. 4 in including the imaging unit 101. However, the endoscope 11 of FIG. 8 is different from that of FIG. 4 in that the sub sensor 121 is newly provided.

Further, in FIG. 8, the CCU 13 includes the frame storage unit 103, the area-of-interest setting unit 104, the normal map generation unit 105, the high-accuracy map generation unit 106, the preoperative information storage unit 107, the display image generation unit 108, and a scene detection unit 131. Therefore, the CCU 13 of FIG. 8 is the same as that of FIG. 4 in including the frame storage unit 103 to the display image generation unit 108. However, the CCU 13 of FIG. 8 is different from that of FIG. 4 in that the scene detection unit 131 is provided instead of the scene detection unit 102.

Herein, in a case where an operative field image that is an RGB image is used to generate a 3D map and a failure occurs in generation of the 3D map using such an RGB operative field image, it is difficult for the normal map generation unit 105 to generate a normal map and perform localization.

For example, in a case where bleeding, smoking, or the like occurs in an operative field during an operation, sufficient feature points of a subject cannot be detected by the Visual SLAM serving as the first algorithm. This makes it difficult to generate a normal map and perform localization. Further, it is difficult to generate a proper 3D map for a part to which blood is attached or a part hidden by smoke.

Therefore, in FIG. 8, the endoscope 11 includes not only the imaging unit 101 serving as a sensor that senses (receives) visible rays of light and outputs an RGB operative field image as a result of the sensing but also the sub sensor 121 that performs sensing under a sensing condition suitable for sensing an obstructive scene. Further, in FIG. 8, the scene detection unit 131 selects the operative field image output by the imaging unit 101 or the sensing result output by the sub sensor 121 depending on whether or not the obstructive scene exists, and outputs the selected result to the frame storage unit 103.

That is, the sub sensor 121 is, for example, a sensor that senses light having a wavelength other than visible rays of light, and outputs a sub sensor image obtained by the sensing as a sensing result.

Therefore, according to the sub sensor image output from the sub sensor 121, a sufficient number of feature points can be detected even in an obstructive scene.

An imaging method and an illumination method used when the sub sensor 121 captures a sub sensor image can be appropriately selected.

For example, in a bleeding scene or a smoking scene, it is possible to employ, as the sub sensor 121, a camera (imaging unit) including a sensor capable of performing transmission observation with infrared (IR), narrow band imaging (NBI), or the like, thereby capturing a sub sensor image by transmission observation using a special light observation technology of illuminating the subject with special light such as IR.

For example, in an overexposure scene, it is possible to employ, as the sub sensor 121, a camera including a polarizing filter such as a polarized light (PL) filter or a neutral density (ND) filter, thereby capturing a sub sensor image in which overexposure is reduced.

The scene detection unit 131, as well as the scene detection unit 102 of FIG. 4, detects an obstructive scene from each frame of the operative field image supplied from the imaging unit 101.

In a case where no obstructive scene is detected, the scene detection unit 131, as well as the scene detection unit 102, outputs the frames of the operative field image (showing no obstructive scene) to the frame storage unit 103.

Further, in a case where the obstructive scene is detected, the scene detection unit 131 outputs, to the frame storage unit 103, a frame of a sub sensor image output by the sub sensor 121 for a frame showing the obstructive scene.

Therefore, for the frame showing the obstructive scene, the frame storage unit 103 can store the frame of the sub sensor image output by the sub sensor 121 as a key frame. As a result, the high-accuracy map generation unit 106 can stably generate a high-accuracy map for the area of interest also in the obstructive scene.

Note that the normal map generation unit 105 can generate a normal map and perform localization by always using an RGB operative field image output by the imaging unit 101, regardless of whether or not the obstructive scene exists. Further, the normal map generation unit 105 can generate a normal map and perform localization by using an RGB operative field image output by the imaging unit 101 in a case where no obstructive scene exists and can generate a normal map and perform localization by using a sub sensor image output by the sub sensor 121 in a case where the obstructive scene exists.

Figure 9:
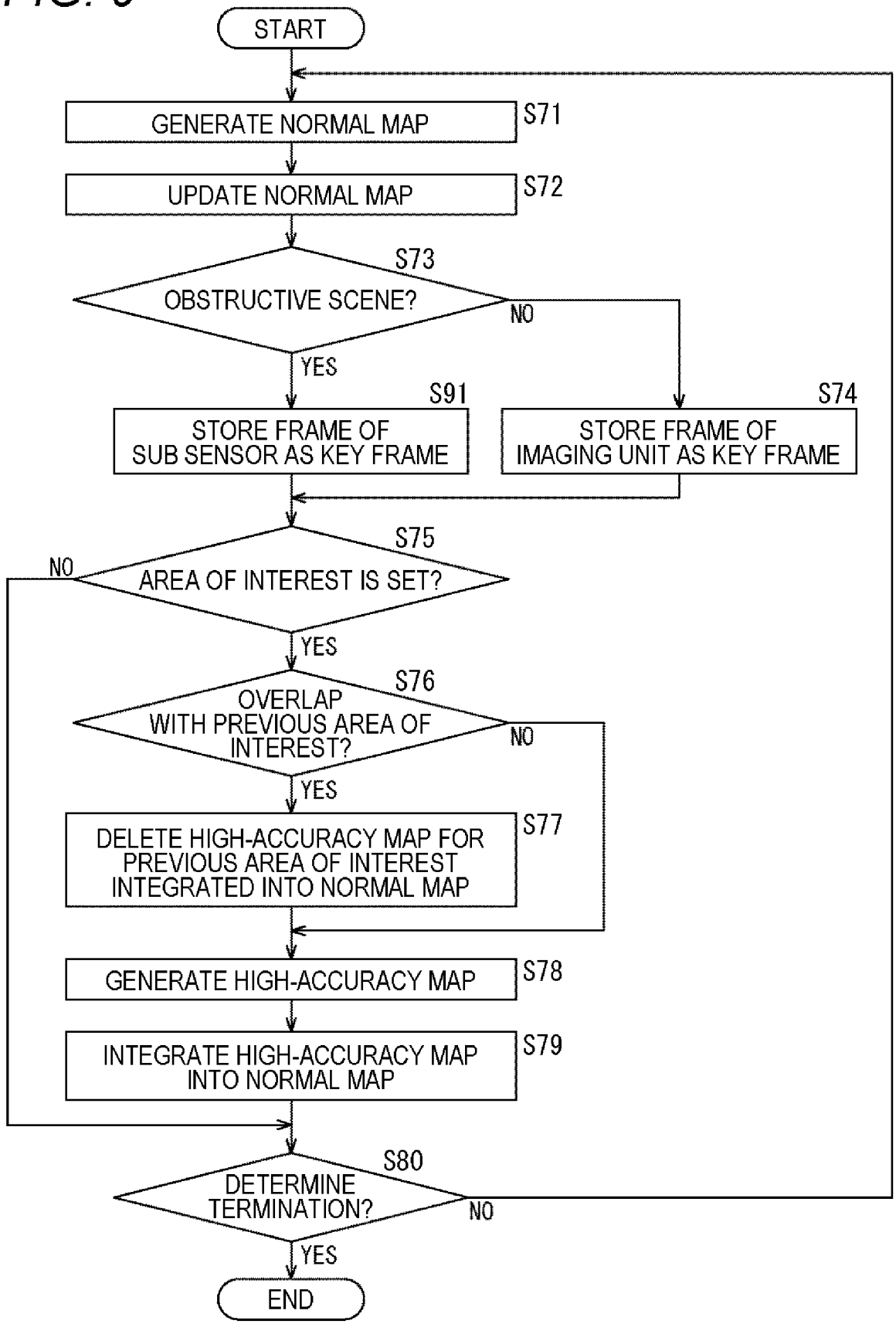
FIG. 9 is a flowchart showing an example of signal processing performed by the CCU 13.

FIG. 9 is a flowchart showing an example of signal processing performed by the CCU 13 of FIG. 8.

In the CCU 13, processing in steps S71 to S74 is performed in a similar manner to that in steps S51 to S54 of FIG. 7.

Then, in step S73 corresponding to step S53 of FIG. 7, in a case where it is determined that the frame of the operative field image output by the imaging unit 101 is an obstructive frame, the processing proceeds to step S91.

In step S91, for the obstructive frame showing an obstructive scene in the operative field image output by the imaging unit 101, the frame storage unit 103 stores a frame of a sub sensor image output by the sub sensor 121 as a key frame as necessary, and the processing proceeds to step S75.

Processing in steps S75 to S80 is performed in similar manner to that in steps S55 to S60 of FIG. 7.

Note that, in FIG. 9, regarding the obstructive scene, the entire frame showing the obstructive scene can be set as the area of interest. In this case, in a case where the obstructive scene is short, it is possible to generate a high-accuracy map that accurately expresses an unclear part in the RGB operative field image caused by the obstruction while maintaining the real-time property.

As described above, a normal map is generated as a 3D map for an operative field with the first algorithm by using an operative field image obtained by imaging the operative field, whereas, in a case where an area of interest is set in the operative field image, a high-accuracy map is generated as a 3D map for the area of interest with the second algorithm different from the first algorithm. Therefore, it is possible to generate a highly accurate 3D map for the area of interest while ensuring the real-time property for generating a 3D map (and performing localization) by employing, for example, a 3D map generation algorithm capable of ensuring the real-time property while having a small amount of calculation as the first algorithm and a generation algorithm capable of generating a highly accurate 3D map as the second algorithm. As a result, it is possible to provide accurate and stable information to the operator as information obtained by using the 3D map.

Further, the sub sensor 121 capable of appropriately sensing the obstructive scene is employed, and therefore, even in a case where the area of interest includes a scene that obstructs generation of a 3D map using an RGB operative field image, such as a bleeding scene or smoking scene, it is possible to generate a highly accurate 3D map for the area of interest.

<Description of Computer to which Present Technology is Applied>

Next, the series of processing of the CCU 13 described above can be executed by hardware or software. In a case where the series of processing is executed by software, a program forming the software is installed in a general-purpose computer or the like.

FIG. 10 is a block diagram illustrating a configuration example of an embodiment of the computer in which the program for executing the series of processing described above is installed.

The program can be recorded in advance on a hard disk 905 or a ROM 903 as a recording medium built in the computer.

Alternatively, the program can be stored (recorded) in a removable recording medium 911 driven by a drive 909. Such a removable recording medium 911 can be provided as so-called packaged software. Herein, examples of the removable recording medium 911 include a flexible disk, a compact disc read only memory (CD-ROM), a magneto optical (MO) disk, a digital versatile disc (DVD), a magnetic disk, and a semiconductor memory.

Note that the program can be installed in the computer from the removable recording medium 911 described above, or can be downloaded to the computer via a communication network or a broadcast network to be installed in the built-in hard disk 905. That is, for example, the program can be wirelessly transferred from a download site to the computer via an artificial satellite for digital satellite broadcasting, or can be transferred by wire to the computer via a network such as a local area network (LAN) or the Internet.

The computer includes a central processing unit (CPU) 902, and the CPU 902 is connected to an input/output interface 910 via a bus 901.

When the user inputs a command via the input/output interface 910 by, for example, operating an input unit 907, the CPU 902 executes a program stored in the read only memory (ROM) 903 in response to the command. Alternatively, the CPU 902 loads a program stored in the hard disk 905 into a random access memory (RAM) 904 and executes the program.

Therefore, the CPU 902 performs the processing according to the flowcharts described above or the processing performed by the configurations of the block diagrams described above. Then, for example, the CPU 902 outputs a result of the processing from an output unit 906, transmits the processing result from a communication unit 908, or records the processing result on the hard disk 905 via the input/output interface 910 as necessary.

Note that the input unit 907 includes a keyboard, a mouse, a microphone, and the like. Further, the output unit 906 includes a liquid crystal display (LCD), a speaker, and the like.

Herein, in the present specification, the processing performed by the computer according to the program is not necessarily performed in time series in the order described in the flowcharts. That is, the processing performed by the computer according to the program also includes processing executed in parallel or individually (e.g., parallel processing or processing performed by an object).

Further, the program may be processed by a single computer (processor) or may be processed in a distributed manner by a plurality of computers. Furthermore, the program may be transferred to a remote computer and be executed therein.

Still further, in the present specification, a system means a set of a plurality of components (devices, modules (parts), and the like), and it does not matter whether or not all the components are included in the same housing. Therefore, a plurality of devices included in separate housings and connected via a network and a single device including a plurality of modules in a single housing are both systems.

Note that the embodiments of the present technology are not limited to the above embodiments, and can be variously modified without departing from the gist of the present technology.

For example, the present technology can have a configuration of cloud computing in which a single function is shared and jointly processed by a plurality of devices via a network.

Further, each of the steps described in the above flowcharts can be executed by a single device, or can be executed by being shared by a plurality of devices.

Furthermore, in a case where a single step includes a plurality of processes, the plurality of processes included in the single step can be executed by a single device, or can be executed by being shared by a plurality of devices.

In addition, the effects described in the present specification are merely examples and are not limited, and additional effects may be exerted.

Note that the present technology can have the following configurations.

<1>

A medical system including:

an imaging unit that images an operative field and outputs an operative field image;

a first generation unit that generates 3D information regarding the operative field with a first algorithm by using the operative field image; and a second generation unit that, in a case where an area of interest is set in the operative field image, generates 3D information regarding the area of interest with a second algorithm different from the first algorithm.

<2>

The medical system according to <1>, in which the second algorithm generates the 3D information having higher accuracy than the 3D information generated by the first algorithm.

<3>

The medical system according to <1> or <2>, further including an integration unit that integrates the 3D information generated by the second algorithm into the 3D information generated by the first algorithm.

<4>

The medical system according to <3>, in which the integration unit aligns the 3D information generated by the second algorithm with the 3D information generated by the first algorithm, and integrates the 3D information generated by the second algorithm into the 3D information generated by the first algorithm.

<5>

The medical system according to <3> or <4>, in which in a case where the area of interest overlaps with a previous area of interest, the integration unit deletes 3D information regarding the previous area of interest integrated into the 3D information generated by the first algorithm and integrates 3D information regarding the area of interest thus newly generated.

<6>
The medical system according to any one of <1> to <5>, in which
the first algorithm is an algorithm that generates the 3D information and performs localization based on the imaging unit.
<7>
The medical system according to any one of <1> to <6>, in which
the first algorithm is Visual-SLAM.
<8>
The medical system according to any one of <1> to <7>, in which
the second algorithm is an algorithm that does not perform localization.
<9>
The medical system according to any one of <1> to <8>, in which
the second algorithm is Multi-view stereo.
<10>
The medical system according to any one of <1> to <9>, in which
the first algorithm has a smaller amount of calculation than the second algorithm.
<11>
The medical system according to any one of <1> to <10>, in which
the second generation unit generates the 3D information with the second algorithm by using a key frame selected from frames of the operative field image output by the imaging unit.
<12>
The medical system according to <11>, further including
a scene detection unit that detects a specific frame showing a specific scene from the frames of the operative field image, in which
the second generation unit generates the 3D information with the second algorithm by using the key frame selected from the frames of the operative field image other than the specific frame.
<13>
The medical system according to <11> or <12>, in which
a frequency of selecting the key frame is switched according to a change in a location of the imaging unit.
<14>
The medical system according to any one of <1> to <13>, further including
an area-of-interest setting unit that sets the area of interest.
<15>
The medical system according to <14>, in which
the area-of-interest setting unit sets the area of interest in response to specification from a user.
<16>
The medical system according to <14> or <15>, in which
the area-of-interest setting unit sets the area of interest in response to output from a predetermined robot.
<17>
The medical system according to any one of <14> to <16>, in which
the area-of-interest setting unit sets an area showing a site specified in advance as the area of interest.
<18>
A signal processing device including:
a first generation unit that generates 3D information regarding an operative field with a first algorithm by using an operative field image obtained by imaging the operative field; and
a second generation unit that, in a case where an area of interest is set in the operative field image, generates 3D information regarding the area of interest with a second algorithm different from the first algorithm
<19>
A signal processing method including:
generating 3D information regarding an operative field with a first algorithm by using an operative field image obtained by imaging the operative field; and
in a case where an area of interest is set in the operative field image, generating 3D information regarding the area of interest with a second algorithm different from the first algorithm

REFERENCE SIGNS LIST

11 Endoscope
13 CCU
15 Display device
17 Light source device
21 Treatment tool device
22 Energy treatment tool
23 Forceps
24 Pneumoperitoneum device
25a, 25b Trocar
26 Recorder
27 Printer
31 Cart
33 Patient bed
35 Foot switch
101 Imaging unit
102 Scene detection unit
103 Frame storage unit
104 Area-of-interest setting unit
105 Normal map generation unit
106 High-accuracy map generation unit
107 Preoperative information storage unit
108 Display image generation unit
121 Sub sensor
131 Scene detection unit
901 Bus
902 CPU
903 ROM
904 RAM
905 Hard disk
906 Output unit
907 Input unit
908 Communication unit
909 Drive
910 Input/output interface
911 Removable recording medium

The invention claimed is:
1. A medical system, comprising:
an imaging sensor configured to:
capture an endoscopic field image associated with an endoscopic field; and
output the endoscopic field image; and
circuitry configured to:
generate, based on a first algorithm and the endoscopic field image, first three-dimensional (3D) information associated with the endoscopic field, wherein
the first 3D information is associated with an entire range of the endoscopic field image;

set a first area of interest in the endoscopic field image; and generate, based on a second algorithm, second 3D information associated with the first area of interest, wherein the second algorithm is different from the first algorithm, and the first area of interest is within the entire range of the endoscopic field image.

2. The medical system according to claim 1, wherein the second 3D information has higher accuracy than the first 3D information.

3. The medical system according to claim 1, wherein the circuitry is further configured to integrate the second 3D information into the first 3D information.

4. The medical system according to claim 3, wherein the circuitry is further configured to:

align the second 3D information with the first 3D information; and integrate the aligned second 3D information into the first 3D information.

5. The medical system according to claim 3, wherein the circuitry is further configured to:

delete third 3D information associated with a second area of interest in the endoscopic field image, in a case where the set first area of interest overlaps with the second area of interest, wherein the second area of interest is set prior to the first area of interest; and integrate, based on the deletion, the second 3D information associated with the first area of interest into the first 3D information.

6. The medical system according to claim 1, wherein the circuitry is further configured to:

perform localization on the entire range of the endoscopic field image based on the first algorithm;

generate the first 3D information based on the performed localization.

7. The medical system according to claim 1, wherein the first algorithm includes a Visual-SLAM algorithm.

8. The medical system according to claim 1, wherein the second algorithm does not perform localization.

9. The medical system according to claim 1, wherein the second algorithm includes a Multi-view stereo algorithm.

10. The medical system according to claim 1, wherein the first algorithm has a smaller amount of calculation than the second algorithm.

11. The medical system according to claim 1, wherein the circuitry is further configured to:

select a key frame from a plurality of frames of the endoscopic field image; and generate the second 3D information based on the selected key frame.

12. The medical system according to claim 11, wherein the circuitry is further configured to:

detect a specific frame from the plurality of frames of the endoscopic field image, wherein the specific frame is associated with a specific scene; and generate, based on the second algorithm, the second 3D information based on the selected key frame other than the specific frame.

13. The medical system according to claim 11, wherein the circuitry is further configured to:

detect a change in a location of the imaging sensor; and switch a frequency to select the key frame based on the detected change in the location of the imaging sensor.

14. The medical system according to claim 1, wherein the circuitry is further configured to set the first area of interest based on specification from a user.

15. The medical system according to claim 1, wherein the circuitry is further configured to:

receive, from a robot, an input associated with a specific area of the endoscopic field image; and set the specific area as the first area of interest based on the input received from the robot.

16. The medical system according to claim 1, wherein the circuitry is further configured to:

obtain information associated with a site to be operated; and set, based on the obtained information, a specific area of the site as the first area of interest.

17. A signal processing device, comprising:

circuitry configured to:

obtain an endoscopic field image associated with an endoscopic field;

generate, based on a first algorithm and the endoscopic field image, first three-dimensional (3D) information associated with the endoscopic field, wherein the first 3D information is associated with an entire range of the endoscopic field image;

set an area of interest in the endoscopic field image; and generate, based on a second algorithm, second 3D information associated with the area of interest, wherein the second algorithm is different from the first algorithm, and the area of interest is within the entire range of the endoscopic field image.

18. A signal processing method, comprising:

obtaining an endoscopic field image associated with an endoscopic field;

generating, based on a first algorithm and the endoscopic field image, first three dimensional (3D) information associated with the endoscopic field, wherein the first 3D information is associated with an entire range of the endoscopic field image;

setting an area of interest in the endoscopic field image; and generating, based on a second algorithm, second 3D information associated with the area of interest, wherein the second algorithm is different from the first algorithm, and the area of interest is within the entire range of the endoscopic field.

19. A medical system, comprising:

an imaging sensor configured to:

capture an endoscopic field image associated with an endoscopic field; and output the endoscopic field image; and circuitry configured to:

generate, based on a first algorithm and the endoscopic field image, first three-dimensional (3D) information associated with the endoscopic field;

generate, based on a second algorithm, second 3D information associated with a first area of interest, in a case where the first area of interest is in the endoscopic operative field image, wherein the second algorithm is different from the first algorithm;

delete third 3D information associated with a second area of interest, in a case where the first area of interest overlaps with the second area of interest, wherein the second area of interest is set prior to the first area of interest; and
integrate, based on the deletion, the second 3D information associated with the first area of interest into the first 3D information.

\* \* \* \* \*